(12) United States Patent
Abdelgany

(10) Patent No.: US 7,608,081 B2
(45) Date of Patent: Oct. 27, 2009

(54) ROD REDUCER

(75) Inventor: Mahmoud F. Abdelgany, Rockaway, NJ (US)

(73) Assignee: Custom Spine, Inc., Parsippany, NJ (US)

( * ) Notice: Subject to any disclaimer, the term of this patent is extended or adjusted under 35 U.S.C. 154(b) by 570 days.

(21) Appl. No.: 11/206,458

(22) Filed: Aug. 18, 2005

(65) Prior Publication Data

US 2006/0293690 A1    Dec. 28, 2006

Related U.S. Application Data

(60) Provisional application No. 60/683,697, filed on May 23, 2005.

(51) Int. Cl.
*A61F 2/00* (2006.01)
(52) U.S. Cl. .................. 606/103; 606/86 A; 606/914; 606/99
(58) Field of Classification Search ............ 606/103, 606/104, 61, 99, 246, 247, 248, 249, 250, 606/251, 252, 253, 254, 255, 256, 257, 258, 606/259, 260, 261, 262, 263, 264, 265, 266, 606/267, 268, 269, 270, 271, 272, 273, 274, 606/275, 276, 277, 278, 279, 96, 86 A, 914, 606/915, 916
See application file for complete search history.

(56) References Cited

U.S. PATENT DOCUMENTS

| 5,020,519 | A |   | 6/1991  | Hayes et al. |         |
|-----------|---|---|---------|--------------|---------|
| 5,312,410 | A | * | 5/1994  | Miller et al.    | 606/86  |
| 5,423,857 | A | * | 6/1995  | Rosenman et al.  | 606/219 |
| 5,480,389 | A | * | 1/1996  | McWha et al.     | 604/165.02 |
| 5,720,751 | A |   | 2/1998  | Jackson |  |
| 5,782,830 | A |   | 7/1998  | Farris |  |
| 5,782,831 | A |   | 7/1998  | Sherman et al. |  |
| 5,910,141 | A |   | 6/1999  | Morrison et al. |  |
| 5,935,133 | A | * | 8/1999  | Wagner et al. | 606/103 |
| 6,036,692 | A |   | 3/2000  | Burel et al. |  |
| 6,123,707 | A |   | 9/2000  | Wagner |  |
| 6,183,472 | B1 |  | 2/2001  | Lutz |  |
| 6,440,133 | B1 |  | 8/2002  | Beale et al. |  |
| 6,565,569 | B1 | * | 5/2003  | Assaker et al. | 606/61 |
| 6,660,006 | B2 |  | 12/2003 | Markworth et al. |  |
| 6,743,231 | B1 | * | 6/2004  | Gray et al. | 606/86 A |
| 6,790,209 | B2 | * | 9/2004  | Beale et al. | 606/61 |
| 2003/0083669 | A1 | * | 5/2003 | Gleason | 606/103 |

(Continued)

*Primary Examiner*—Eduardo C Robert
*Assistant Examiner*—Jan Christopher Merene
(74) *Attorney, Agent, or Firm*—Rahman LLC

(57) ABSTRACT

A cam coupling rod reducer and method of operation comprises an inner tube comprising a first end having a hole and a second end having a plurality of prongs extending therefrom. The rod reducer further includes a lever cam connected to the first end, wherein the lever cam comprises a base and a pair of semicircular arms extending from the base, wherein each of the arms comprise a hole configured to align with the hole of the first end of the inner tube. The rod reducer also includes an outer extension tube connected to the inner tube, wherein the outer extension tube comprises positional markings on the body of the outer extension tube; a top end having a concave opening; and a bottom end comprising an opening configured to permit the prongs of the inner tube to extend therethrough; and a pair of pegs extending from the bottom end.

20 Claims, 16 Drawing Sheets

U.S. PATENT DOCUMENTS

| | | |
|---|---|---|
| 2003/0176875 A1* | 9/2003 | Anderson et al. ............ 606/151 |
| 2005/0149048 A1* | 7/2005 | Leport et al. ................... 606/99 |
| 2005/0261702 A1* | 11/2005 | Oribe et al. ................. 606/103 |
| 2006/0036254 A1* | 2/2006 | Lim ............................ 606/86 |
| 2007/0167954 A1* | 7/2007 | Sicvol et al. ................ 606/104 |
| 2007/0282337 A1* | 12/2007 | Garamszegi ................. 606/53 |

* cited by examiner

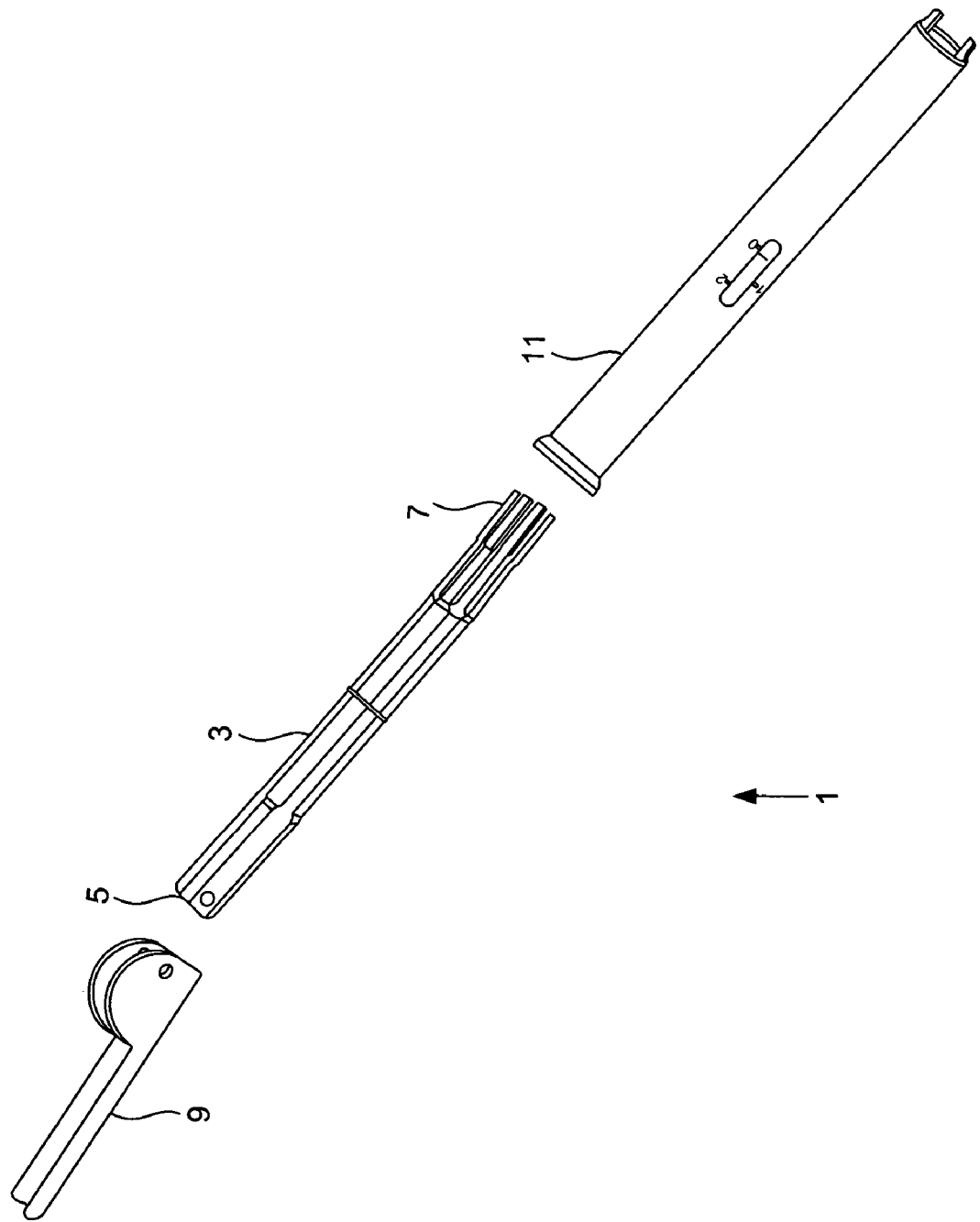

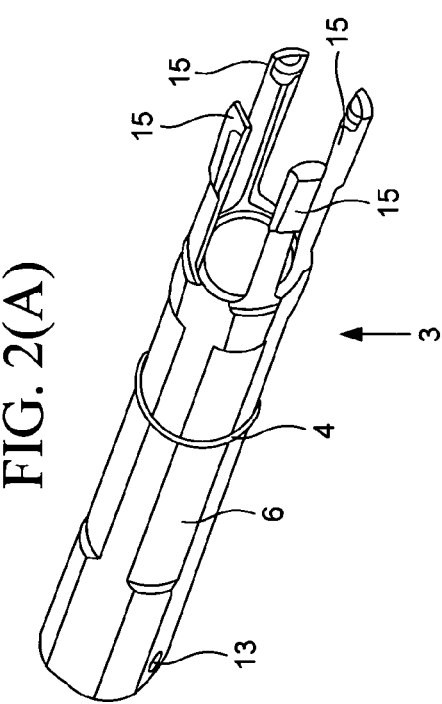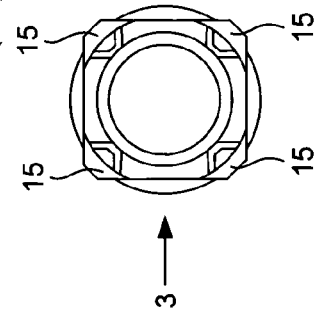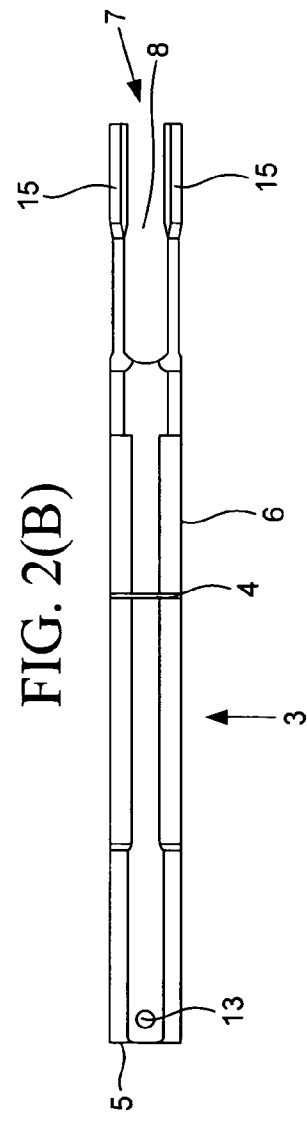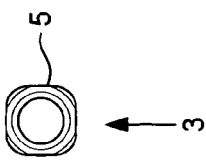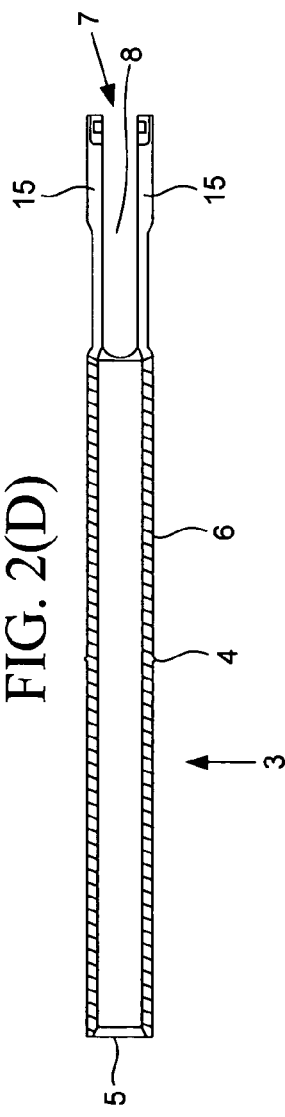

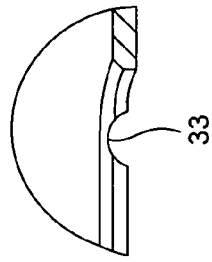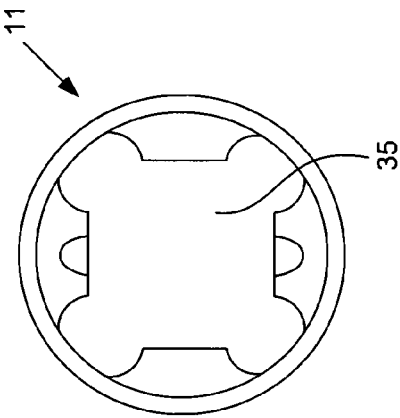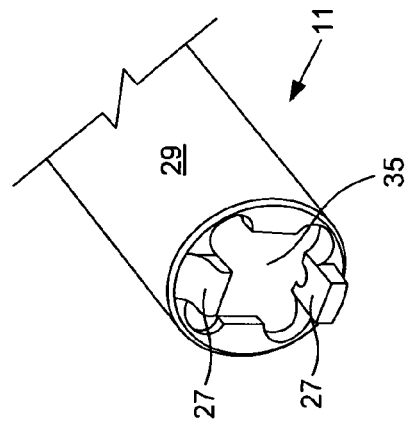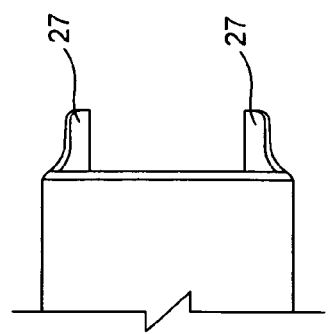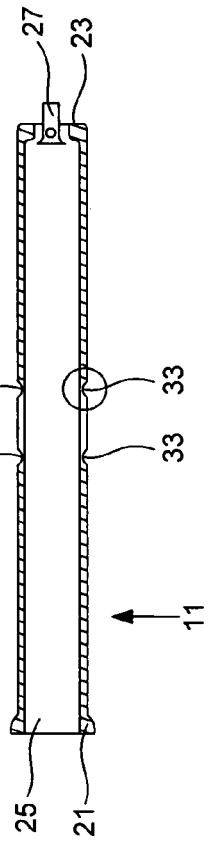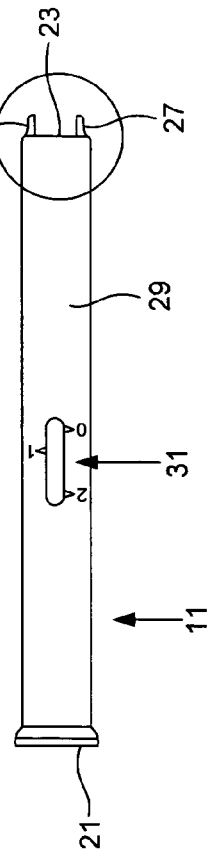

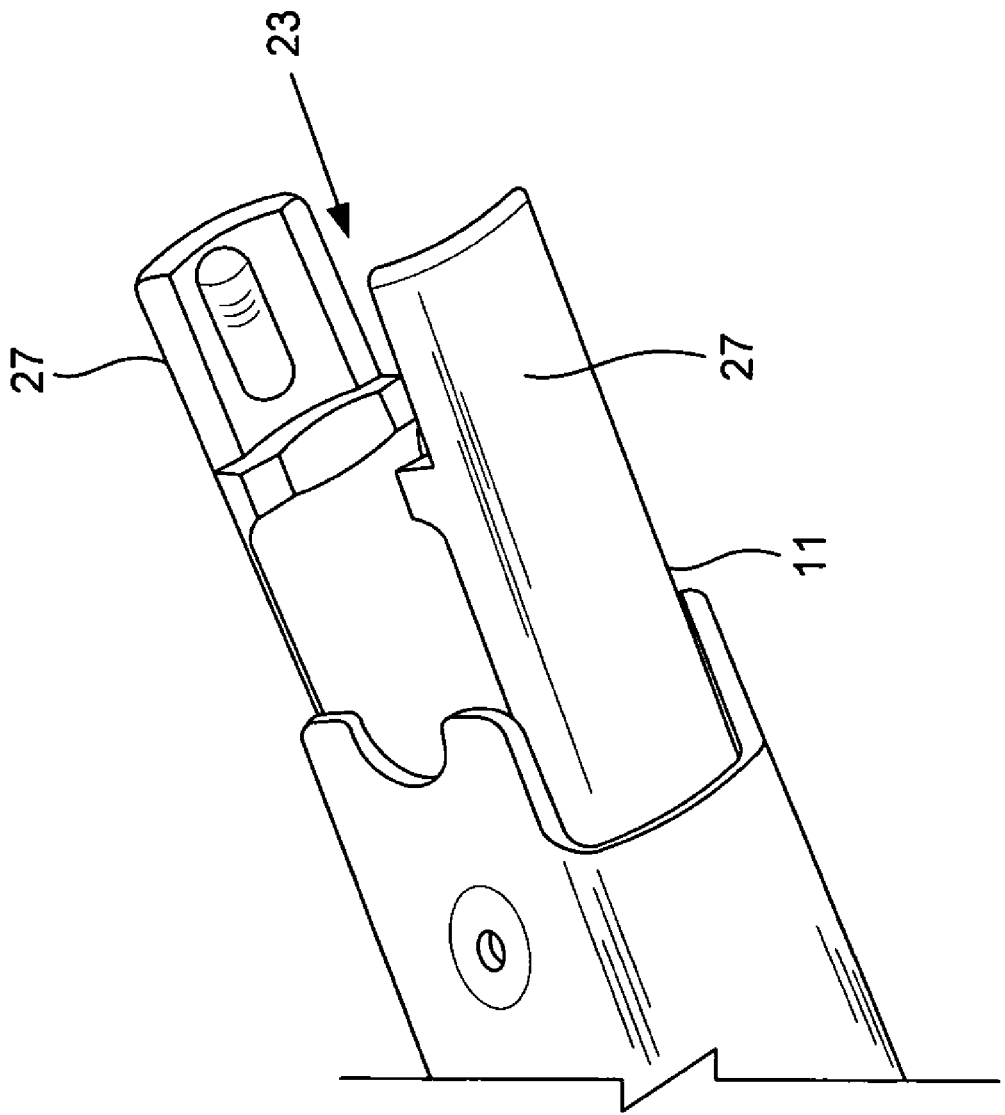

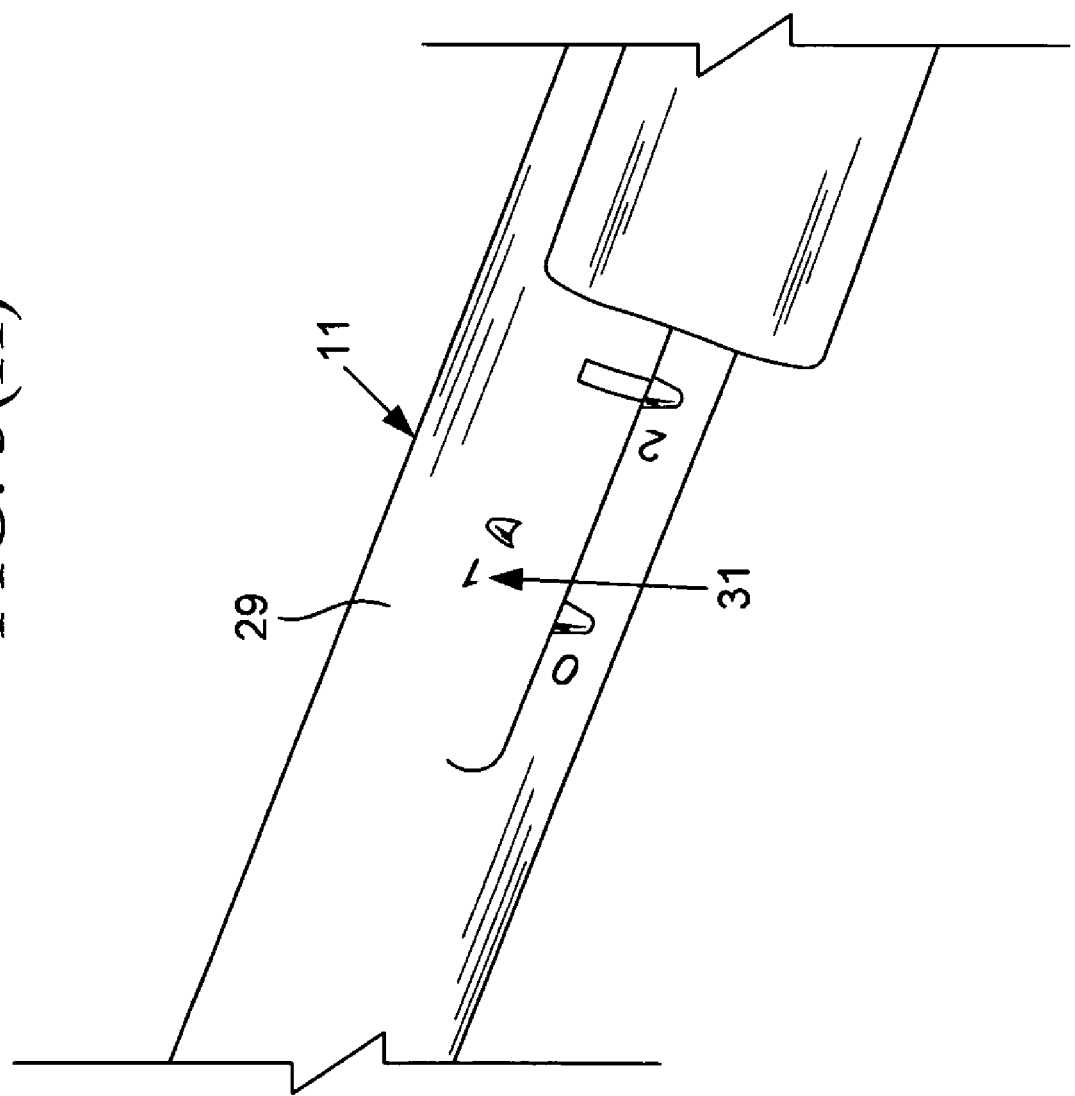

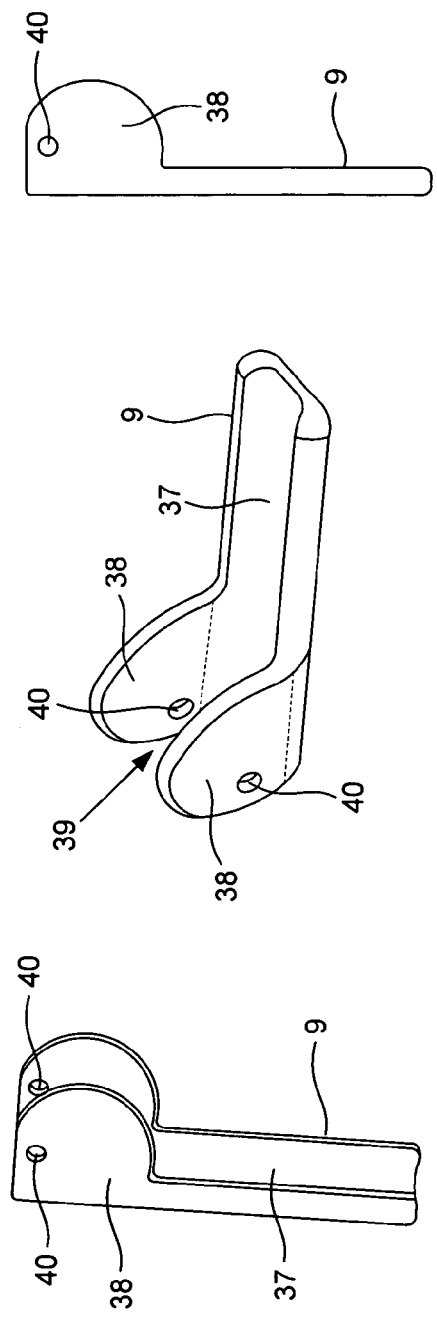

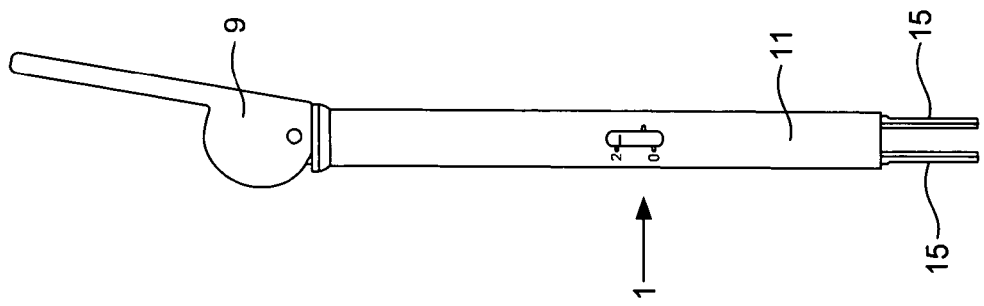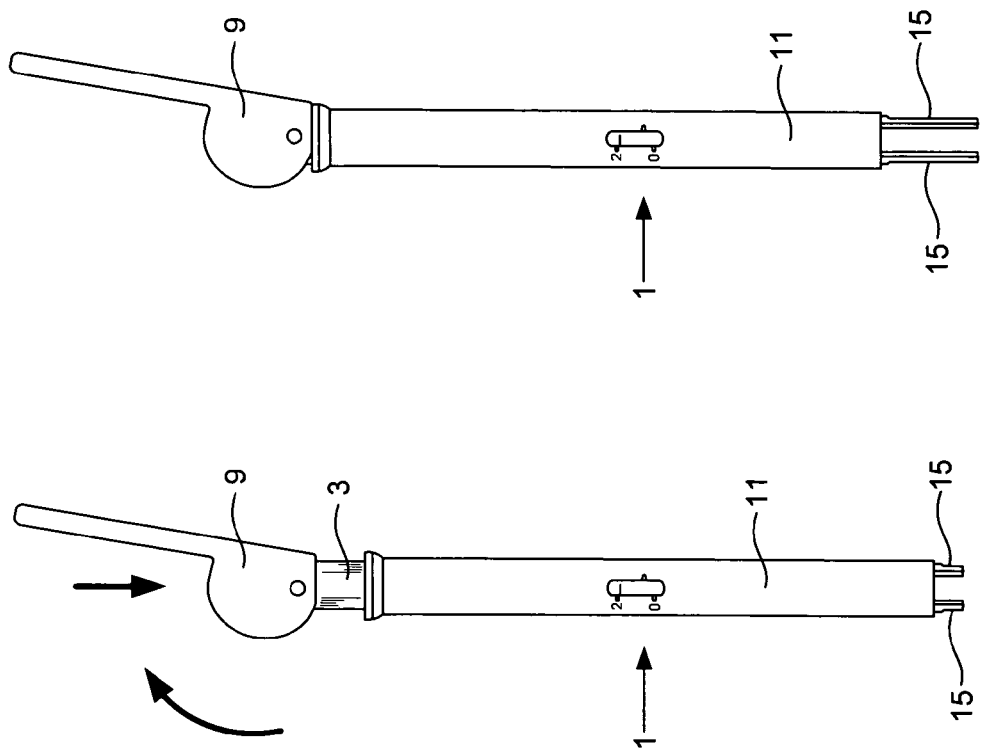

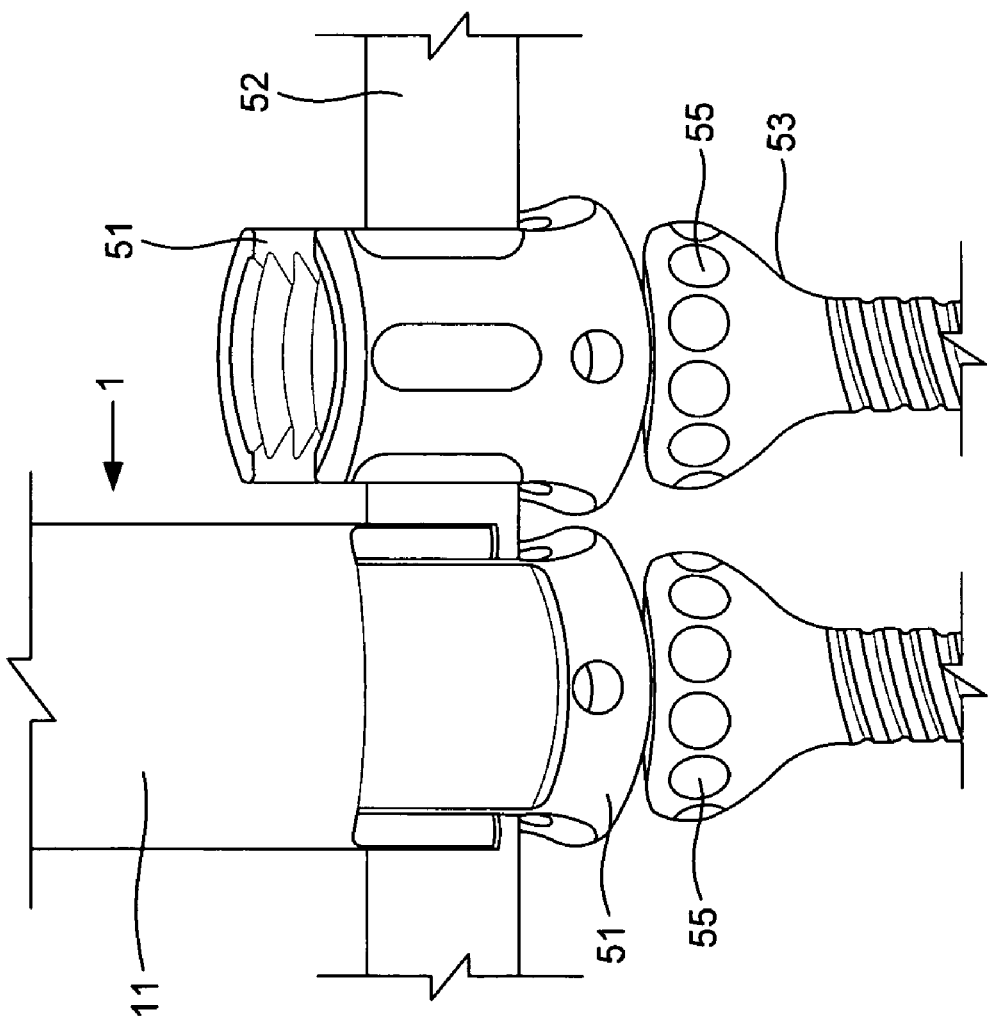

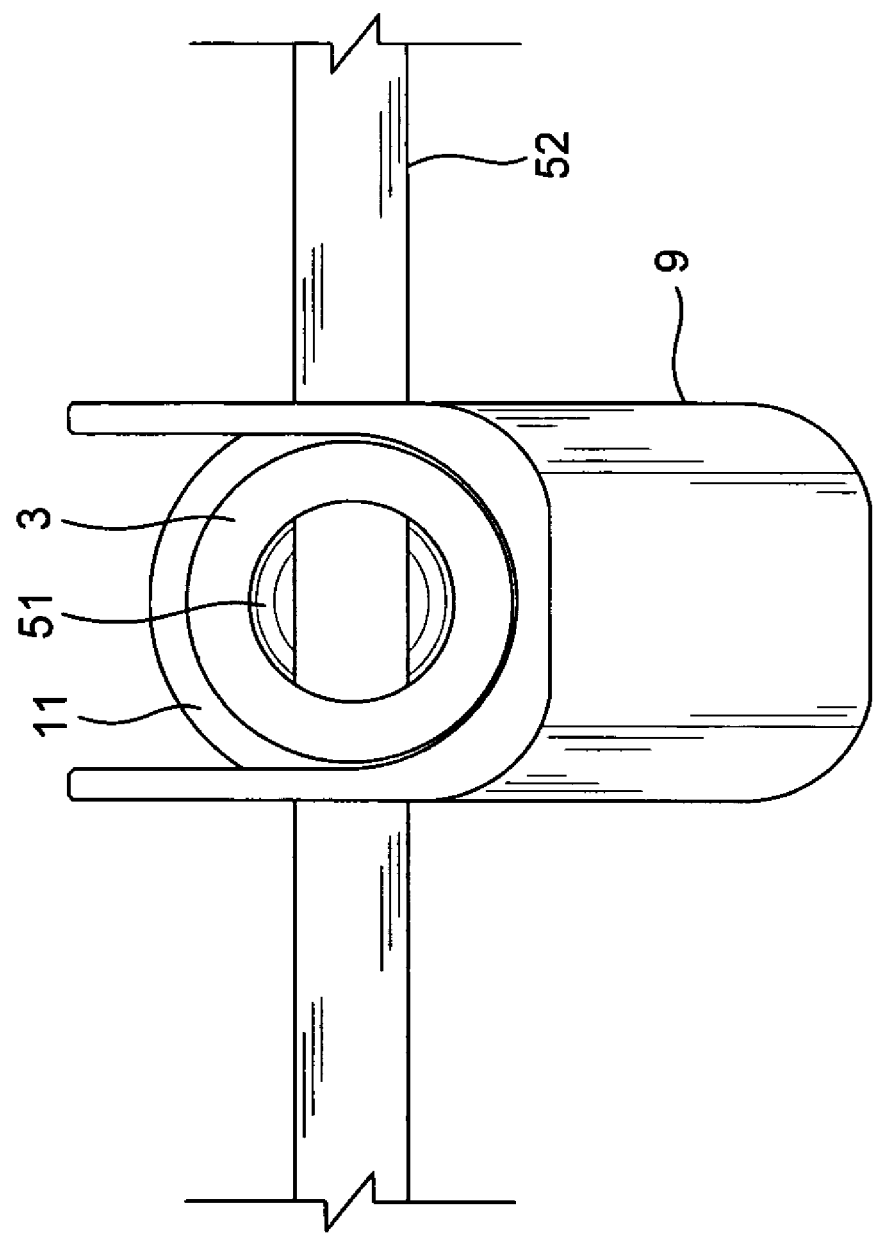

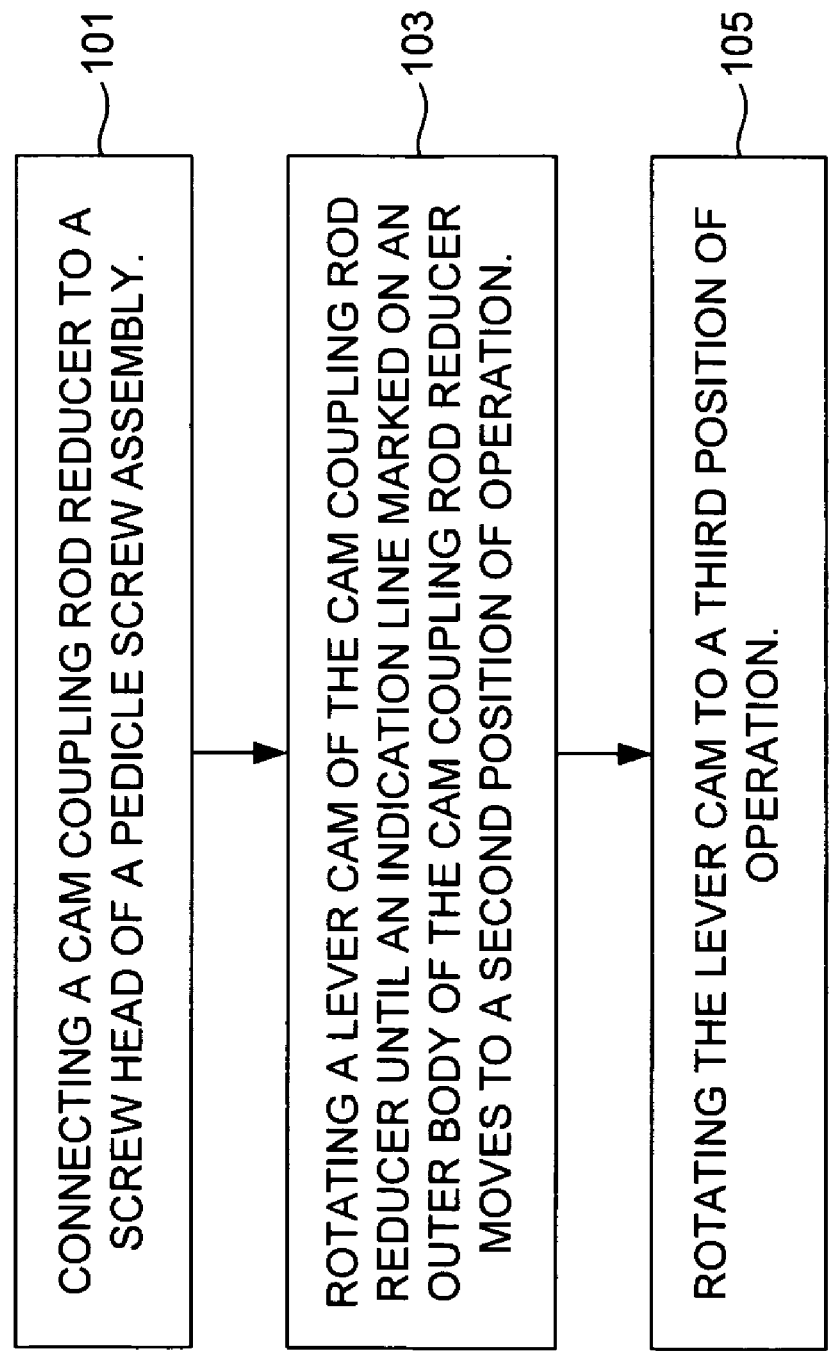

ROD REDUCER

CROSS REFERENCE TO RELATED APPLICATION

This application claims the benefit of U.S. Provisional Patent Application No. 60/683,697 filed on May 23, 2005, the contents of which in its entirety is herein incorporated by reference.

BACKGROUND

1. Field of the Invention

The embodiments of the invention generally relate to medical devices, and, more particularly, to medical devices for use in spinal surgeries.

2. Description of the Related Art

Most conventional rod reducers are typically bulky and/or require two hands to properly operate. Furthermore, the conventional solutions are generally bereft of a viable solution for rod reduction when L5-S1 implants are very close together or touching to reduce spondylothesis during spinal deformity surgeries. As such, most conventional rod reducers tend to suffer from the following attributes: (1) they are generally too bulky and not minimally invasive surgery (MIS) compatible; (2) they generally require two handed operation; (3) they typically require too much space in the medial or lateral direction and interfere with the facet or the transverse process; and (4) they tend to apply too much force through a threaded mechanism, which does not allow for tactile sensation. This could result in the possibility of the bone anchor in a pedicle screw assembly being pulled out of the anatomy during operation. Therefore, there remains a need for a novel rod reducer device capable of reducing spondylothesis during spinal deformity surgeries, and generally overcoming the limitations of the conventional devices.

SUMMARY

In view of the foregoing, an embodiment of the invention provides a cam coupling rod reducer comprising an inner tube; a lever cam connected to the inner tube; and an outer extension tube connected to the inner tube, wherein the outer extension tube comprises positional markings on an outer surface of the outer extension tube. Preferably, the inner tube comprises a first end having a hole; and a second end having a plurality of prongs extending therefrom. Moreover, the lever cam is preferably connected to the first end of the inner tube. Additionally, the lever cam preferably comprises a base; and a pair of semicircular arms spaced apart and parallel to one another and extending from the base, wherein each of the arms comprise a hole dimensioned and configured to align with the hole of the first end of the inner tube. Preferably, the outer extension tube comprises a top end having a concave opening; and a bottom end opposite to the top end. The bottom end may comprise an opening dimensioned and configured to permit the prongs of the inner tube to extend therethrough; and a pair of pegs extending from the bottom end in a direction substantially similar to a direction of the prongs extending from the second end of the inner tube. The outer extension tube may comprise indent features defined in an outer body of the outer extension tube. Furthermore, the inner tube may comprise a rib circumferentially disposed around a body of the inner tube.

Another embodiment of the invention provides a method of persuading a spinal rod into a top loading spinal implant assembly, wherein the method comprises connecting a cam coupling rod reducer to a screw head of a pedicle screw assembly, wherein spaces in between prongs at a second end of an inner tube of the rod reducer are positioned parallel to a rod of the pedicle screw assembly, and wherein the connection of the cam coupling rod reducer to the screw head indicates a first position of operation; rotating a lever cam of the cam coupling rod reducer until an indication line marked on an outer body of the cam coupling rod reducer moves to a second position of operation; and rotating the lever cam to a third position of operation, wherein the third position of operation indicates that the rod is optimally seated in the pedicle screw assembly, and that the pedicle screw assembly is ready to accept a blocker screw. Preferably, the cam coupling rod reducer comprises an inner tube; the lever cam connected to the inner tube; and an outer extension tube connected to the inner tube, wherein the outer extension tube comprises positional markings on an outer surface of the outer extension tube. The inner tube may comprise a first end having a hole; and a second end having a plurality of prongs extending therefrom. Preferably, the lever cam is connected to the first end of the inner tube. The lever cam may comprise a base; and a pair of semicircular arms spaced apart and parallel to one another and extending from the base, wherein each of the arms comprise a hole dimensioned and configured to align with the hole of the first end of the inner tube. Preferably, the outer extension tube comprises a top end having a concave opening; and a bottom end opposite to the top end. Furthermore, the bottom end may comprise an opening dimensioned and configured to permit the prongs of the inner tube to extend therethrough; and a pair of pegs extending from the bottom end in a direction substantially similar to a direction of the prongs extending from the second end of the inner tube. Preferably, the outer extension tube comprises indent features defined in an outer body of the outer extension tube. Moreover, the inner tube may comprise a rib circumferentially disposed around a body of the inner tube.

These and other aspects of the embodiments of the invention will be better appreciated and understood when considered in conjunction with the following description and the accompanying drawings. It should be understood, however, that the following descriptions, while indicating preferred embodiments of the invention and numerous specific details thereof, are given by way of illustration and not of limitation. Many changes and modifications may be made within the scope of the embodiments of the invention without departing from the spirit thereof, and the embodiments of the invention include all such modifications.

BRIEF DESCRIPTION OF THE DRAWINGS

The embodiments of the invention will be better understood from the following detailed description with reference to the drawings, in which:

FIG. 1 illustrates an exploded view of a cam coupler according to an embodiment of the invention;

FIGS. 2(A) through 2(E) illustrate schematic diagrams of the cam coupler inner tube of the cam coupler of FIG. 1 according to an embodiment of the invention;

FIGS. 3(A) through 3(H) illustrate schematic diagrams of the cam coupler outer extension (persuader) of the cam coupler of FIG. 1 according to an embodiment of the invention;

FIGS. 4(A) through 4(E) illustrate schematic diagrams of the cam coupler lever cam of the cam coupler of FIG. 1 according to an embodiment of the invention;

FIGS. 5(A) through 5(D) illustrate schematic diagrams of the cam coupler of FIG. 1 in various stages of manipulation according to an embodiment of the invention;

FIGS. 6(A) through 6(F) illustrate schematic diagrams of the cam coupler of FIG. 1 in use in a surgical environment according to an embodiment of the invention; and FIG. 7 is a flow diagram illustrating a preferred method according to an embodiment of the invention.

DETAILED DESCRIPTION OF PREFERRED EMBODIMENTS

Figure 5C:
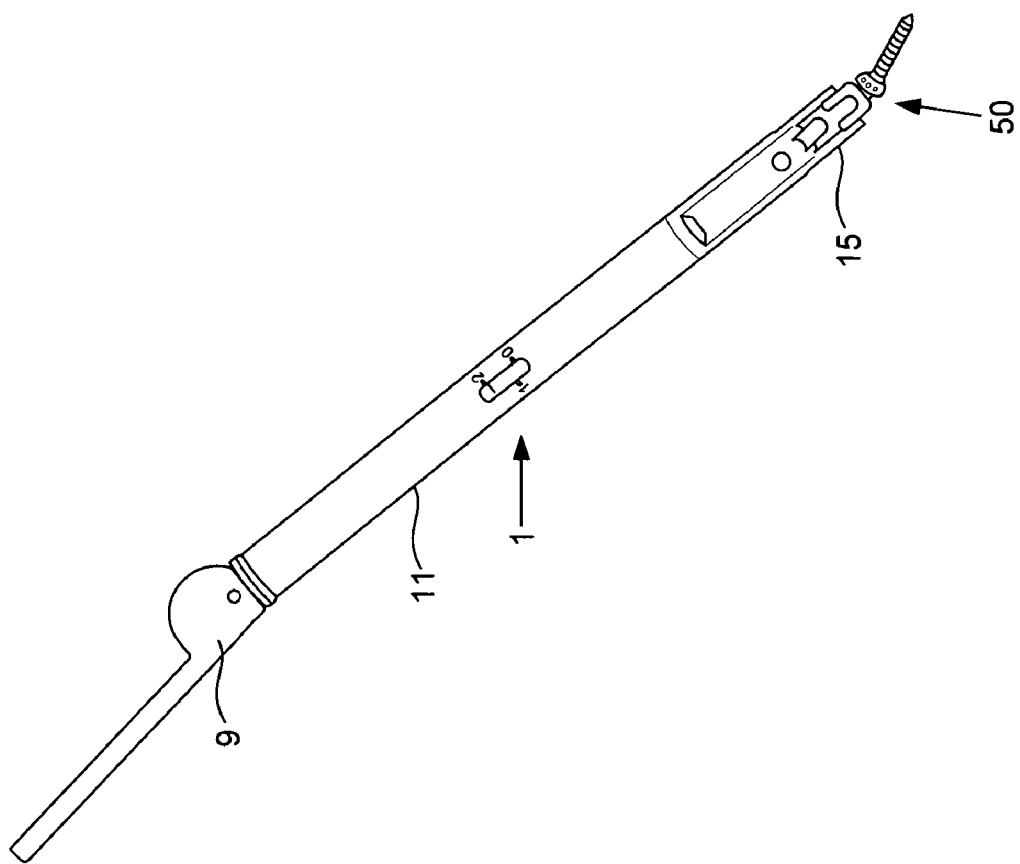

The embodiments of the invention and the various features and advantageous details thereof are explained more fully with reference to the non-limiting embodiments that are illustrated in the accompanying drawings and detailed in the following description. It should be noted that the features illustrated in the drawings are not necessarily drawn to scale. Descriptions of well-known components and processing techniques are omitted so as to not unnecessarily obscure the embodiments of the invention. The examples used herein are intended merely to facilitate an understanding of ways in which the embodiments of the invention may be practiced and to further enable those of skill in the art to practice the embodiments of the invention. Accordingly, the examples should not be construed as limiting the scope of the embodiments of the invention.

As mentioned, there remains a need for a novel rod reducer device capable of reducing spondylothesis during spinal deformity surgeries, and generally overcoming the limitations of the conventional devices. The embodiments of the invention achieve this by providing a cam action rod reducer to persuade a spinal rod into a top loading spinal implant. The cam mechanism towards the top of the instrument actually performs the reduction of the rod (therefore pulling the slipped vertebral body back up in place and relieving the pressure on the nerves). Referring now to the drawings, and more particularly to FIGS. 1 through 7, where similar reference characters denote corresponding features consistently throughout the figures, there are shown preferred embodiments of the invention.

FIG. 1 illustrates an exploded view of a cam coupler 1 according to an embodiment of the invention. Generally, the cam coupler 1 comprises an inner tube 3 comprising a first end 5 and a second end 7 distally located along a same longitudinal axis from one another. The cam coupler 1 further includes a lever cam 9 connected to the first end 5 of the inner tube 3, and an outer extension (persuader) 11 connected to the second end 7 of the inner tube 3. The lever cam 9 rotatably mounts to the inner tube 3 via a dowel pin (not shown). Furthermore, the outer extension, 11 which is preferably hollow, slidably mounts over the inner tube 3.

FIGS. 2(A) through 2(E) illustrate schematic diagrams of the cam coupler inner tube 3 of the cam coupler 1 of FIG. 1 according to an embodiment of the invention. The first end 5 of the inner tube 3 includes a hole 13 dimensioned and configured to receive a dowel pin (not shown) for attachment to the lever cam 9 (of FIG. 1). Preferably, the inner tube 3 is generally elongated and has an overall cylindrical shape. Preferably, the inner tube 3 is hollow. The second end 7 of the inner tube 3 terminates with a plurality of equally spaced prongs 15. Preferably, there are four prongs 15. However, the embodiments of the invention are not limited to a particular number of prongs 15. The prongs 15 are positioned in a generally circular manner so as to continue the overall cylindrical contour of the inner tube 3 from its first end 5 to the second end 7. Moreover, the inner tube 4 may comprise a rib 4 circumferentially disposed around a body 6 of the inner tube 3. The rib 4 functions as an indicator and lines up with the indent features 33 of the outer surface 29 of the outer extension 11 as shown in FIGS. 3(A) through 3(H), and further described below.

FIGS. 3(A) through 3(H) illustrate schematic diagrams of the cam coupler outer extension (persuader) 11 of the cam coupler 1 of FIG. 1 according to an embodiment of the invention. The outer extension (persuader) 11 generally includes two ends 21, 23; the top end 21 has a generally concave opening 25 and the bottom end 23 terminates with a pair of extension pegs 27. Furthermore, the bottom end 23 is dimensioned and configured to allow the prongs 15 of the second end 7 of the inner tube 3 (of FIGS. 2(A) through 2(E)) to extend therethrough. Preferably, the bottom end 23 includes a clover-shaped hole 35, which accommodates the prongs 15 of the second end 7 of the inner tube 3 (of FIGS. 2(A) through 2(E)). The top and bottom ends 21, 23 are distally located along a longitudinal axis from one another. The outer surface 29 of the outer extension 11 also includes markings 31 with the indication lines described above. The outer surface 29 of the outer extension 11 further includes indent features 33 defined therein. Generally, the indent features 33 serve as indicators to guide a user as to which stage of operation the instrument is undergoing (i.e., from position "0" to position "1", etc. as further described below). FIG. 3(D) is an enlarged view of the encircled portion of FIG. 3(F). FIG. 3(C) is an enlarged view of the encircled portion of FIG. 3(E). FIG. 3(G) illustrates an alternate embodiment of the bottom end 23 of the outer extension 11 with the pair of extension pegs 27 shown in an elongated configuration. FIG. 3(H) illustrates an alternate view of the positional markings 31 on the outer surface 29 of the outer extension 11.

FIGS. 4(A) through 4(E) illustrate schematic diagrams of the cam coupler lever cam 9 of the cam coupler 1 of FIG. 1 according to an embodiment of the invention. The lever cam 9 generally comprises an elongated base 37 with a pair of semicircular arms 38 extending from one end 39 of the base 37. The arms 38 are generally parallel to each other and are separated by a channel 39 defined by the width of the base 37. Each of the arms 38 includes holes 40, which are dimensioned and configured to align with the hole 13 of the inner tube 3 (of FIGS. 2(A) through 2(D)) through which a dowel pin (not shown) may extend for rotatable mounting of the lever cam 9 to the inner tube 3. Thus, once the lever cam 9 is mounted onto the inner tube 3, it can articulate in various degrees of rotation with respect to the inner tube 3.

Figure 5D:
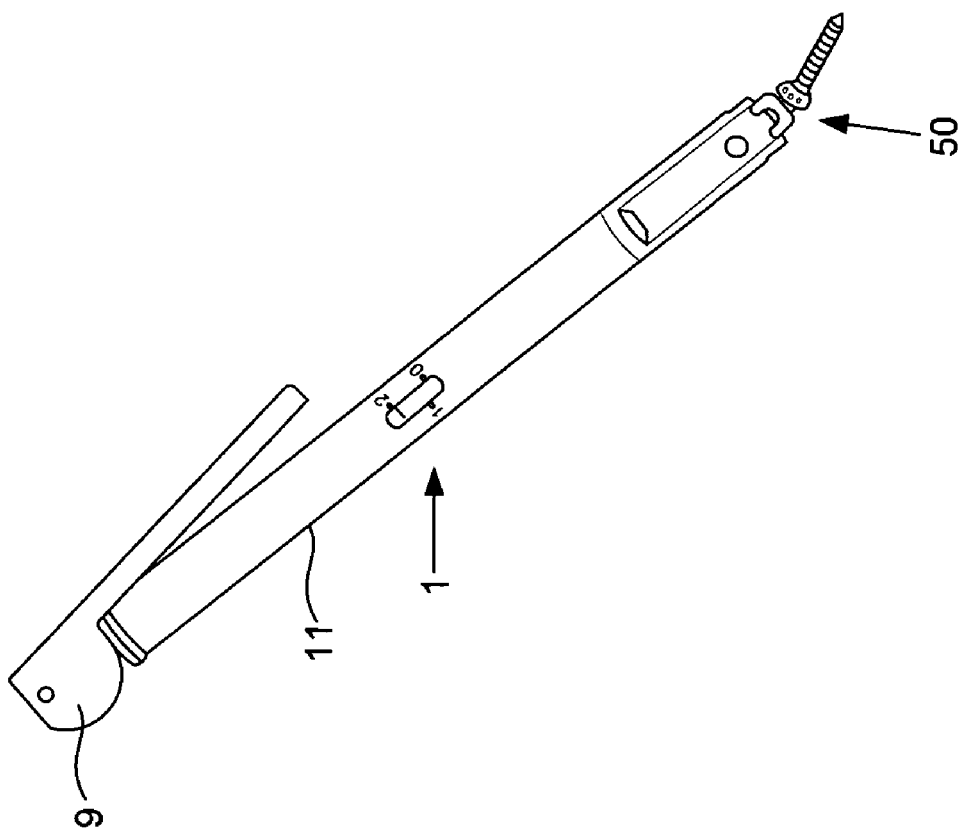

FIGS. 5(A) through 5(D) illustrate schematic diagrams of the cam coupler 1 of FIG. 1 in various stages of manipulation according to an embodiment of the invention. FIGS. 5(A) and 5(B) illustrate the attached lever cam 9 and inner tube 3 components being slidably mounted in the outer extension 11. FIGS. 5(C) and 5(D) illustrate the cam coupler 1 attaching to a pedicle screw assembly 50, such as the pedicle screw assembly described in U.S. patent application Ser. Nos. 11/045,908 entitled "Polyaxial Pedicle Screw Assembly", 11/048,189 entitled "Medialised Rod Pedicle Screw Assembly", and 11/048,213 entitled "Biased Angle Polyaxial Pedicle Screw Assembly", the complete disclosures of which, in their entireties are herein incorporated by reference. FIG. 5(C) illustrates the lever cam 9 in the open position. FIG. 5(D) illustrates the lever cam 9 in the closed position. In the open position, the prongs 15 of the inner tube 3 are kept within the boundaries of the outer extension 11. However, once the lever cam 9 is moved into the closed position, the prongs 15 of the inner tube 3 begin to extend through the bottom end 23 of the outer extension 11.

Figure 6A:
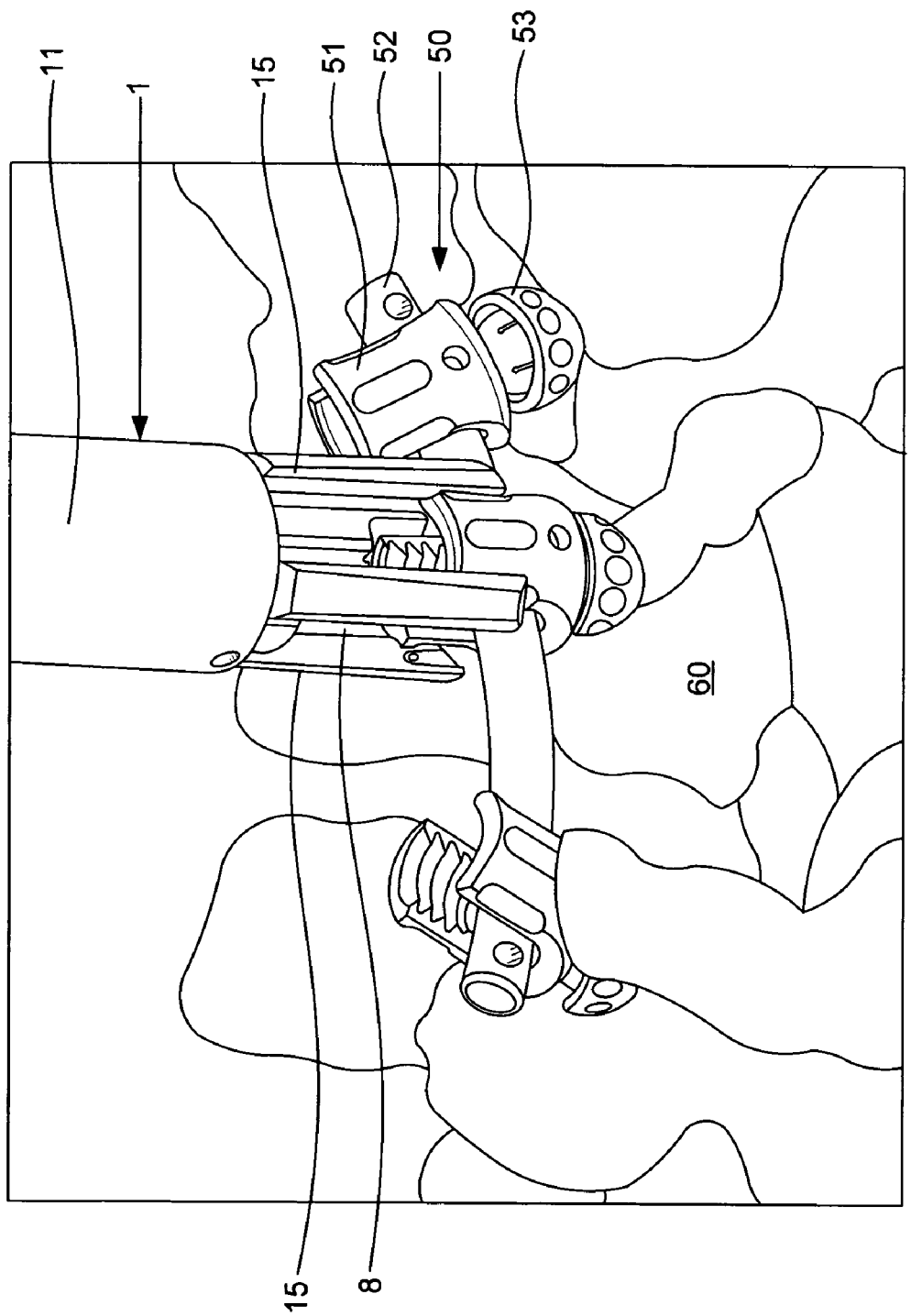
Figure 6B:
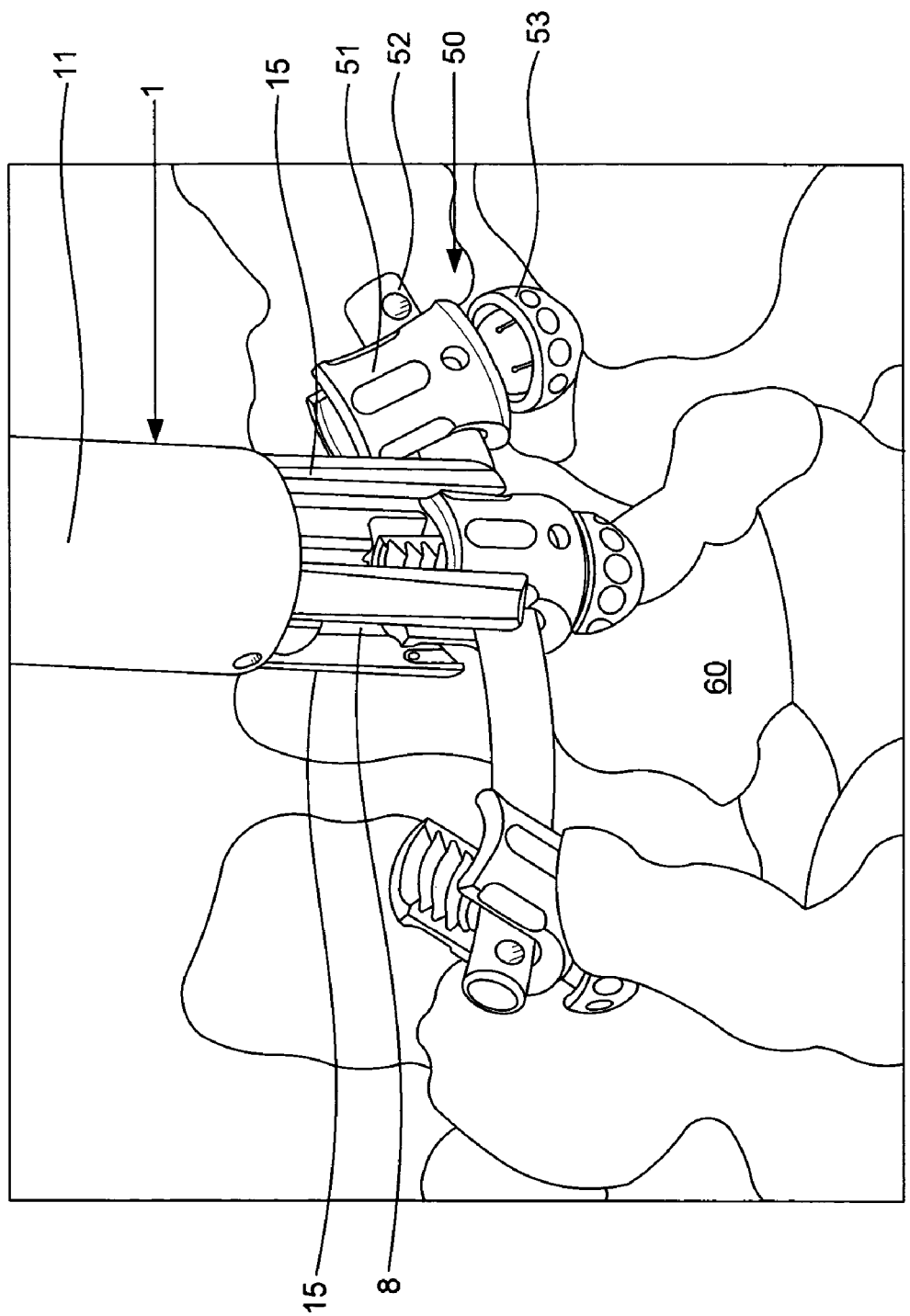
Figure 6C:
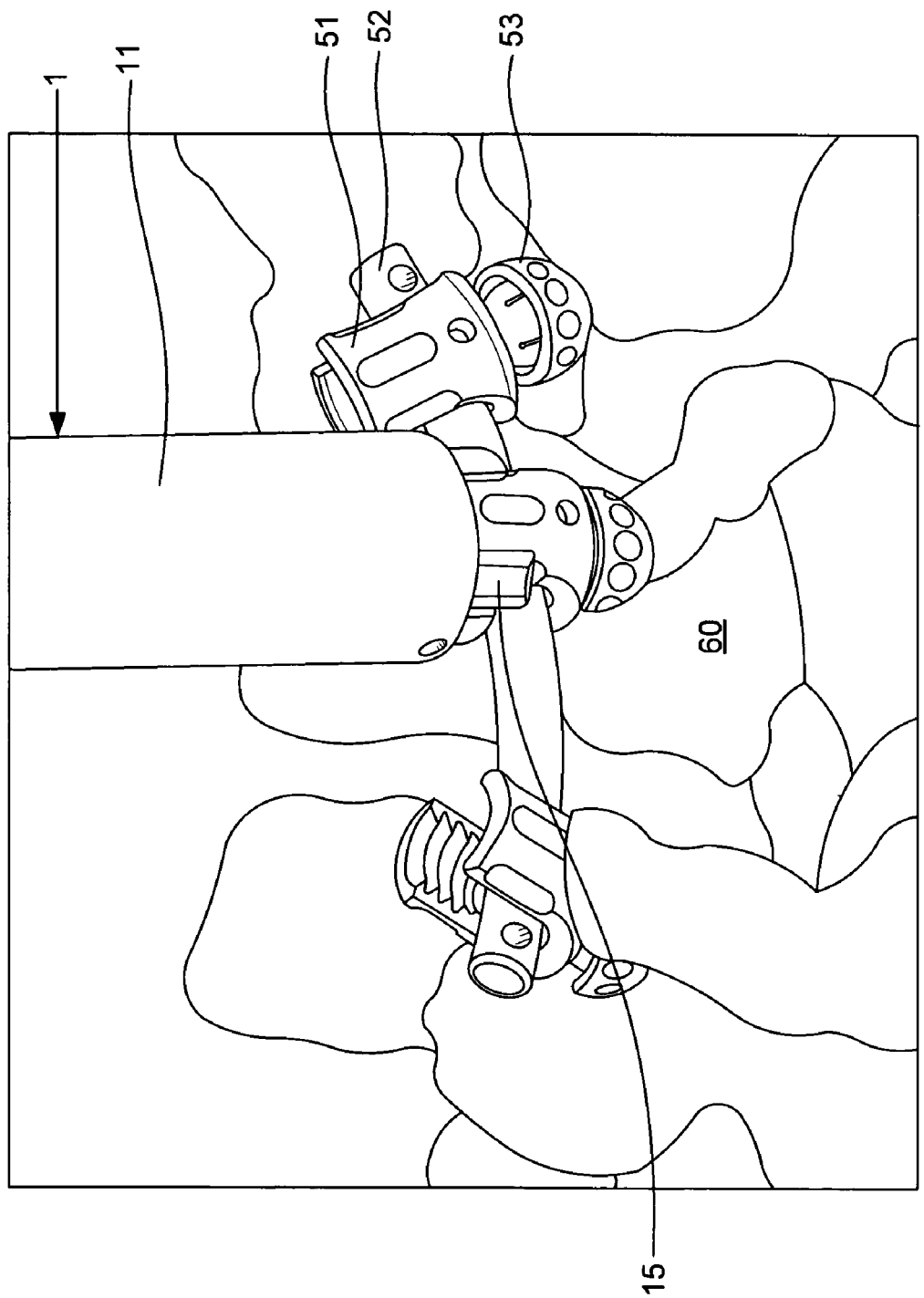
Figure 6D:
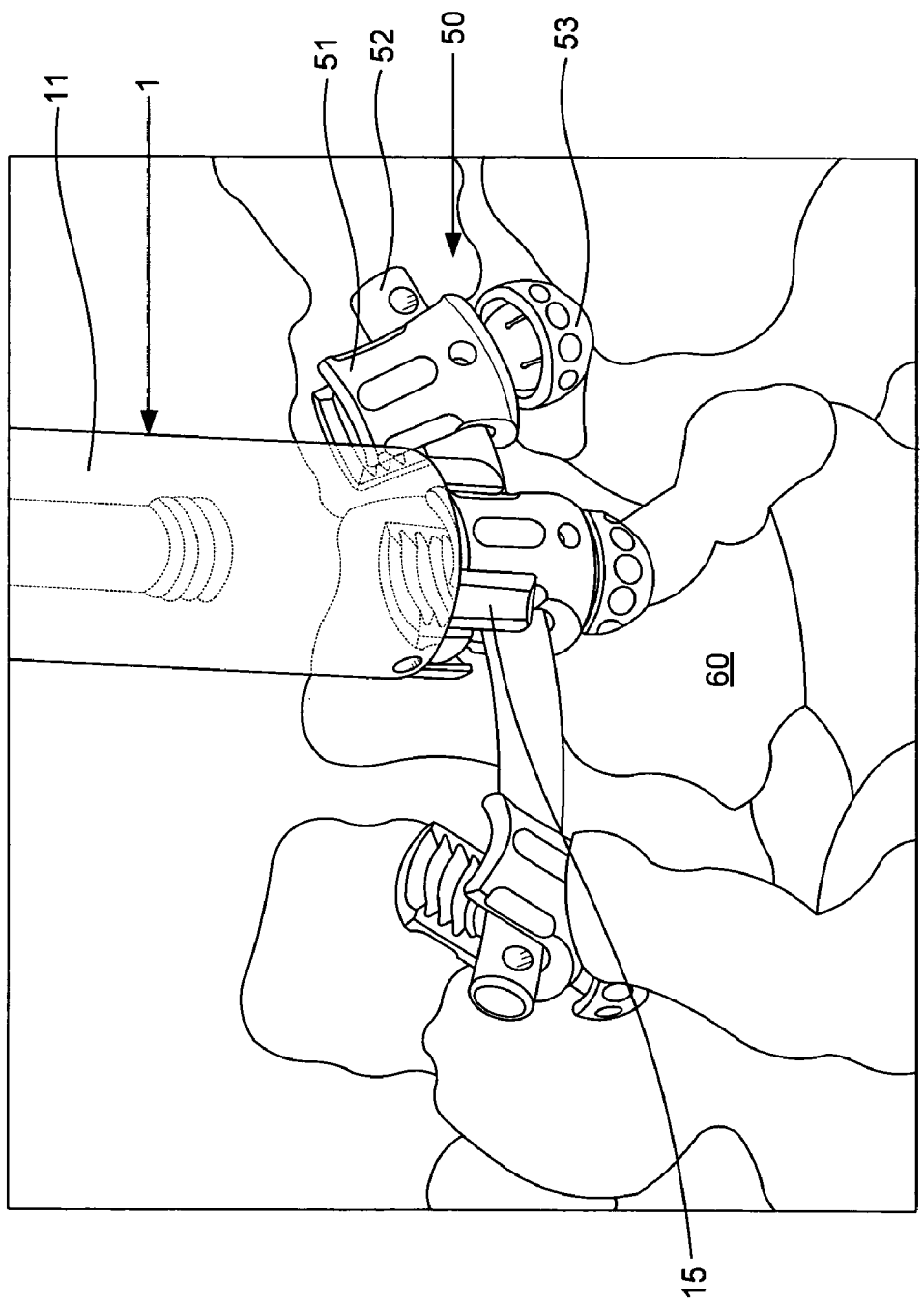

FIGS. 6(A) through 6(F) (with reference to FIGS. 1 through 5(D)) illustrate schematic diagrams of the cam coupler 1 of FIG. 1 in use in a surgical environment (i.e., used to manipulate a screw assembly 50 into a bone 60) according to an embodiment of the invention. FIGS. 6(A) and 6(B) illustrate the cam coupler 1 in the open position and semi-attached position (position '0' moving to position '1'). FIGS. 6(C) and 6(D) generally illustrate the cam coupler 1 in the semi-attached position and fully attached position (position '1' moving to position '2'). In position '0', the rod reducer 1 is connected to the screw head 51. To ensure proper alignment to the screw head 51, the spaces 8 in between the prongs 15 at the second end 7 of the inner tube 3 are preferably parallel to the rod 52. Next, the cam lever 9 (not shown in FIGS. 6(A) through 6(F)) is rotated until the indication line (markings 31) on the outer 29 of the extension tube 11) moves to position '1'. The rod reducer 1 is now firmly attached to the screw head 51 and does not disassemble if properly constructed. Thereafter, the cam lever 9 is fully rotated to position '2'. At this point, the rod 52 is now optimally seated and the pedicle screw 50 assembly is ready to accept a blocker screw (not shown). FIG. 6(E) illustrates an example of how the cam coupler 1 of FIG. 1 may engage a screw head 51 (which attaches to a bone anchor 53) of a pedicle screw assembly 50. FIG. 6(F) illustrates a top view of the screw head 51 with the rod 52 driven down inside of the screw head 51 as they are engaged by the inner tube 3 and extension tube 11 with the lever cam 9.

FIG. 7, with reference to FIGS. 1 through 6(F) is a flow chart illustrating a method of persuading a spinal rod into a top loading spinal implant assembly according to an embodiment of the invention, wherein the method comprises connecting (101) a cam coupling rod reducer 1 to a screw head 51 of a pedicle screw assembly 50, wherein spaces 8 in between the prongs 15 at the second end 7 of the inner tube 3 are positioned parallel to a rod 52 of the pedicle screw assembly 50, and wherein the connection of the cam coupling rod reducer 1 to the screw head 51 indicates a first position of operation; rotating (103) a lever cam 9 of the cam coupling rod reducer 1 until an indication line 31 marked on an outer body 29 of the cam coupling rod reducer 1 moves to a second position of operation; and rotating (105) the lever cam 9 to a third position of operation, wherein the third position of operation indicates that the rod 52 is optimally seated in the pedicle screw assembly 50, and that the pedicle screw assembly 50 is ready to accept a blocker screw (not shown).

The embodiments of the invention may be used to reduce spondylothesis during a spine surgery. This is accomplished by pulling a bone anchor 53 from a pedicle screw assembly 50 to a spinal rod 52 seated in an adjacent bone anchor 53. This function utilizes the positive locating and gripping features 55 on the bone anchors 53. The cam coupling rod reducer 1 provided by the embodiments of the invention may be used when additional force is needed to bring the screw head 51 of a pedicle screw assembly 50 up to the rod 52.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments of the invention have been described in terms of preferred embodiments, those skilled in the art will recognize that the embodiments of the invention can be practiced with modification within the spirit and scope of the appended claims.

What is claimed is:

1. A cam coupling rod reducer comprising: an inner tube comprising:
   an inner hollow area;
   a cylindrical body portion comprising a closed end and an open end positioned opposite to said closed end and along the same longitudinal axis as said closed end, wherein said closed end comprises a through hole extending an entire width of said body portion, and wherein said cylindrical body portion circumferentially surrounds an entirety of said inner hollow area in between said open end and said through hole;
   a plurality of prongs extending outwardly from said body portion and along the same longitudinal axis as said body portion, wherein said plurality of prongs extend from said body portion at a position where said open end of said body portion is located;
   an annular rib circumferentially disposed around an entirety of said body portion;
   a lever cam pivotally connected to a tip of said closed end of said inner tube, wherein said lever cam comprises:
      an elongated base that articulates said lever cam 180 degrees; and
      a pair of semicircular arms spaced apart and parallel to one another and extending from said base, wherein each of said arms comprise exactly one hole that aligns with said through hole of said closed end of said inner tube such that said pair of semicircular arms straddle an entire width of said body portion;
   a cylindrical outer extension tube positioned around said inner tube, wherein said outer extension tube comprises:
      a concave end that contacts said lever cam during articulation of said elongated base; and
      a length equal to at least three-quarters of the length of said inner tube,
   wherein said outer extension tube comprises a tip end positioned opposite to said concave end, and wherein said tip end of said outer extension tube comprises a clover-shaped hole that permits said plurality of prongs of said inner tube to extend therethrough.

2. The cam coupling rod reducer of claim 1, wherein said outer extension tube comprises positional markings on an outer surface of said outer extension tube.

3. The cam coupling rod reducer of claim 1, wherein said tip end of said outer extension tube comprises exactly two pegs extending outwardly from said tip end.

4. The cam coupling rod reducer of claim 1, wherein said tip end of said outer extension tube comprises:
   a pair of pegs extending from said tip end in a direction substantially similar to a direction of said prongs extending from said inner tube.

5. The cam coupling rod reducer of claim 1, wherein said outer extension tube comprises indent features defined in an outer body of said outer extension tube.

6. The cam coupling rod reducer of claim 1, wherein said outer extension tube comprises a slot.

7. The cam coupling rod reducer of claim 6, wherein said annular rib is visible through said slot when said inner tube is seated in said outer extension tube.

8. The cam coupling rod reducer of claim 6, wherein said annular rib is positioned in a substantially midway position of said body portion of said inner tube.

9. A cam coupling rod reducer comprising: a one-piece inner tube comprising:
   an inner hollow area;
   a cylindrical body portion comprising a closed end and an open end positioned opposite to said closed end and along the same longitudinal axis as said closed end, wherein said closed end comprises a through hole extending an entire width of said body portion, and wherein" said cylindrical body portion circumferentially surrounds an entirety of said inner hollow area in between said open end and said through hole;

a plurality of prongs extending outwardly from said body portion and along the same longitudinal axis as said body portion, wherein said plurality of prongs extend from said body portion at a position where said open end of said body portion is located;

an annular rib circumferentially disposed around an entirety of said body portion, wherein said annular rib is positioned in a substantially midway position of said body portion of said inner tube;

a one-piece lever cam pivotally connected to a tip of said closed end of said inner tube, wherein said lever cam is completely external to said inner tube and comprises:

an elongated base that articulates said lever cam 180 degrees; and a pair of semicircular arms spaced apart and parallel to one another and extending from said base, wherein each of said arms comprise exactly one hole that aligns with said through hole of said closed end of said inner tube such that said pair of semicircular arms straddle an entire width of said body portion;

a one-piece cylindrical outer extension tube positioned around said inner tube, wherein said outer extension tube comprises:

a concave end that contacts said lever cam during articulation of said elongated base;

a length equal to at least three-quarters of the length of said inner tube; and a slot positioned in a substantially midway position of said outer extension tube, wherein said outer extension tube comprises a tip end positioned opposite to said concave end, and wherein said tip end of said outer extension tube comprises a clover-shaped hole that permits said plurality of prongs of said inner tube to extend therethrough.

10. The cam coupling rod reducer of claim 9, wherein said outer extension tube comprises positional markings on an outer surface of said outer extension tube.

11. The cam coupling rod reducer of claim 9, wherein said tip end of said outer extension tube comprises exactly two pegs extending outwardly from said tip end.

12. The cam coupling rod reducer of claim 9, wherein said tip end of said outer extension tube comprises:

a pair of pegs extending from said tip end in a direction substantially similar to a direction of said prongs extending from said inner tube.

13. The cam coupling rod reducer of claim 9, wherein said outer extension tube comprises indent features defined in an outer body of said outer extension tube.

14. The cam coupling rod reducer of claim 9, wherein said annular rib is visible through said slot when said inner tube is fully seated in said outer extension tube.

15. A cam coupling rod reducer comprising:

an inner tube comprising:

a hollow inner region;

a first end having a hole;

an open second end having a plurality of prongs extending therefrom;

a body portion that completely wraps around said hollow inner region in an area between said hole and said open second end; and a rib circumferentially disposed around an entire portion of a body of said inner tube;

a lever cam connected to said first end of said inner tube, wherein said lever cam comprises:

a base; and a pair of semicircular arms spaced apart and parallel to one another and extending from said base, wherein each of said arms comprise a hole that aligns with said hole of said first end of said inner tube; and an outer extension tube connected to said inner tube, wherein said outer extension tube comprises:

a slot;

positional markings on a body of said outer extension tube and positioned adjacent to said slot;

indent features defined in said body of said outer extension tube;

a top end having a concave opening; and a bottom end opposite said top end, said bottom end comprising:

a clover-shaped opening that permits said prongs of said inner tube to extend therethrough; and a pair of pegs extending from said bottom end in a direction substantially similar to a direction of said prongs extending from said second end of said inner tube.

16. The cam coupling rod reducer of claim 15, wherein said rib is visible through said slot when said inner tube is seated in said outer extension tube.

17. The cam coupling rod reducer of claim 15, wherein said outer extension tube comprises a length equal to at least three-quarters of the length of said inner tube.

18. The cam coupling rod reducer of claim 15, wherein said slot is positioned in a substantially midway position of said outer extension tube.

19. The cam coupling rod reducer of claim 15, wherein said rib is positioned in a substantially midway position of said body portion of said inner tube.

20. The cam coupling rod reducer of claim 15, wherein said lever cam is pivotally connected to said first end of said inner tube.

* * * * *